(12) United States Patent
Luk et al.

(10) Patent No.: US 6,221,867 B1
(45) Date of Patent: Apr. 24, 2001

(54) 4,5-PYRAZINOXINDOLES

(75) Inventors: Kin-Chun Luk, North Caldwell, NJ (US); Christophe Michoud, New York, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/464,534

(22) Filed: Dec. 15, 1999

Related U.S. Application Data

(60) Provisional application No. 60/112,653, filed on Dec. 17, 1998.

(51) Int. Cl.[7] .................. C07D 241/36; A61K 31/498
(52) U.S. Cl. ..................... 514/250; 544/343; 544/345
(58) Field of Search ................... 544/345, 343; 514/250

(56) References Cited

U.S. PATENT DOCUMENTS

| | | | |
|---|---|---|---|
| 4,556,672 | 12/1985 | Kadin ................... | 514/414 |
| 4,730,003 | 3/1988 | von der Saal et al. ........ | 514/387 |
| 5,206,261 | 4/1993 | Kawaguchi et al. ......... | 514/418 |
| 5,322,950 | 6/1994 | Sircar et al. ............. | 548/253 |
| 5,374,652 | 12/1994 | Buzzetti et al. .......... | 514/418 |
| 5,397,787 | 3/1995 | Buzzetti et al. .......... | 514/300 |
| 5,409,949 | 4/1995 | Buzzetti et al. .......... | 514/414 |
| 5,488,057 | 1/1996 | Buzzetti et al. .......... | 514/312 |
| 5,576,330 | 11/1996 | Buzzetti et al. .......... | 514/307 |
| 5,792,783 | 8/1998 | Tang et al. .............. | 514/397 |
| 5,834,504 | 11/1998 | Tang et al. .............. | 514/418 |
| 5,883,113 | 3/1999 | Tang et al. .............. | 514/418 |
| 5,883,116 | 3/1999 | Tang et al. .............. | 514/418 |
| 5,886,020 | 3/1999 | Tang et al. .............. | 514/418 |
| 5,965,600 | 10/1999 | Sato et al. .............. | 514/419 |
| 5,977,103 | 11/1999 | Adams et al. ............. | 514/235.2 |

FOREIGN PATENT DOCUMENTS

| | | |
|---|---|---|
| 0436333 A2 | 12/1990 | (EP) . |
| 0580502 A1 | 7/1993 | (EP) . |
| WO 97/25986 | 7/1997 | (JP) . |
| WO 92/07830 | 5/1992 | (WO) . |
| WO 95/01349 | 1/1995 | (WO) . |
| WO 96/00226 | 1/1996 | (WO) . |
| WO 96/16964 | 6/1996 | (WO) . |
| WO 96/22976 | 8/1996 | (WO) . |
| WO 96/32380 | 10/1996 | (WO) . |
| WO 96/40116 | 12/1996 | (WO) . |
| WO 97/11692 | 4/1997 | (WO) . |
| WO 97/16447 | 5/1997 | (WO) . |
| WO 97/45409 | 12/1997 | (WO) . |
| WO 97/46551 | 12/1997 | (WO) . |
| WO 98/07695 | 2/1998 | (WO) . |
| 98/07695 * | 2/1998 | (WO) . |
| WO 98/24432 | 6/1998 | (WO) . |
| WO 98/50356 | 11/1998 | (WO) . |
| WO 99/10325 | 3/1999 | (WO) . |
| WO 99/15500 | 4/1999 | (WO) . |
| WO 99/48868 | 9/1999 | (WO) . |
| WO 00 08202 | 2/2000 | (WO) . |

OTHER PUBLICATIONS

Abstract Acc. No. 94–028085/199404 (Abstract of EP 0580502).
Sun et al., J. Med. Chem., 41:2588–2603 (1998).
Sun et al., "Synthesis and Biological Evaluation of Novel 3–[(Substituted pyrrol–2–yl) methylidenyl] indolin–2–ones as Potent and Selective Inhibitors of the Flk–1/KDR Receptor Tyrosine Kinase", Abstract presented at Trip Report: ACS National Meeting, Dallas, Texas, Apr. 1998.
Mohammadi et al., Science, 276:955–960 (May 9, 1997).
Tournier et al., Proceedings of the National Academy of Sciences USA, 94:7337–7342 (Jul. 1997).

* cited by examiner

Primary Examiner—Mukund J. Shah
Assistant Examiner—Hong Liu
(74) Attorney, Agent, or Firm—George W. Johnston; Patricia S. Rocha-Tramaloni

(57) ABSTRACT

Disclosed are novel 4,5-pyrazinoxindoles having the formula

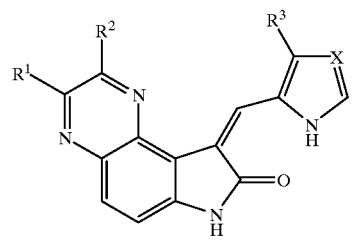

These compounds inhibit or modulate protein kinases, in particular JNK protein kinases. These compounds and their pharmaceutically acceptable salts, and prodrugs of said compounds, are useful as anti-inflammatory agents, particularly useful in the treatment of rheumatoid arthritis. Also disclosed are pharmaceutical compositions containing such compounds, and methods for the treatment and/or control of inflammation, particularly in the treatment or control of rheumatoid arthritis, using these compounds.

16 Claims, No Drawings

4,5-PYRAZINOXINDOLES

This application claims the benefit of U.S. Provisional Application Ser. No. 60/112,653, filed on Dec. 17, 1998.

FIELD OF THE INVENTION

The present invention is directed to novel 4,5-pyrazinoxindoles which inhibit or modulate protein kinases, in particular JNK protein kinases. These compounds and their pharmaceutically acceptable salts, and prodrugs of said compounds, are useful as anti-inflammatory agents, particularly useful in the treatment of rheumatoid arthritis. The invention is also directed to pharmaceutical compositions containing such compounds, and to methods for the treatment and/or control of inflammation, particularly in the treatment or control of rheumatoid arthritis. This invention is further directed to intermediates useful in the preparation of the foregoing compounds.

BACKGROUND OF THE INVENTION

Protein kinases are a class of proteins that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

The JNK (Jun N-terminal kinase) protein kinases (also know as "stress-activated protein kinases" or "SAPK") are members of the mitogen-activated protein (MAP) kinases. See, e.g., S. Gupta et al., EMBO J., vol. 15 no. 11 (1996) pp. 2760–2770; and Yang et al., Nature, vol. 289 (Oct 23, 1997) pp. 865–870. At least ten JNK isoforms are currently known. See, Gupta, id. As its name indicates, one of the substrates for JNK is c-Jun. JNK phosphorylates the $NH_2$-terminal activation domain of c-Jun on Ser63 and Ser73, causing increased c-Jun transcriptional activity. See Gupta, id. In turn, c-Jun is an AP-1 transcription factor that mediates immediate-early gene expression. See, e.g., A. Minden et al., Biochimica et Biophysica Acta 1333 (1997) F85–F104; and A. Karin, Biochimica et Biophysica Acta, vol. 172 (1991) pp. 129–157.

The JNK protein kinase is markedly activated in response to treatment of cells with pro-inflammatory cytokines or exposure to environmental stress. JNK thus mediates the effect of extracellular stimuli on c-Jun. See Gupta, supra; and Minden, supra. Accordingly, JNK is a physiological regulator of AP-1 transcriptional activity. Thus, inhibition of JNK activity will inhibit AP-1-dependent transcription of inflammatory and immune mediators which are implicated in pathological proliferative conditions, for example inflammatory diseases and neuro-degenerative diseases, in particular, rheumatoid arthritis. See, eg. Swantek et al., Molecular and Cellular Biology, vol. 17 (1997) pp. 6274–6282; Maroney et al., J. Neuroscience, vol. 18 (Jan. 1, 1998) pp. 104–111; and Minden, supra, at F92.

The rat homologue of JNK is also called SAPK (stress-activated protein kinase). SAPK isoforms share significant (>90%) sequence identity with the corresponding JNK isoforms [compare Kyriakis et al., Nature, Vol. 369 (May 12, 1994) pp. 156–160 and Gupta et al., supra]. Both JNK and SAPK are capable of phosphorylation of the cJun substrate and thus have very similar enzyme activity. JNK and SAPK are part of a protein kinase cascade that is activated by various extracellular stimuli. See e.g. Minden supra; and Kyriakis et al., BioEssays Vol. 18 (1996) pp. 567–577. JNK and SAPK each can be activated by phosphorylation on specific threonine and tyrosine residues by dual specificity MAP kinase kinases such as MKK4, SEK-1, or MKK7. See Kyriakis et al., supra; and Tournier et al., Proceedings of the National Academy of Sciences USA Vol. 94 (July 1997), pp. 5 7337–7342). The dual specificity MAP kinase kinases can be activated by phosphorylation on serine and/or threonine residues by MAP kinase kinases such as MEKK-1. Thus, measurement of JNK or SAPK enzyme activity may be enhanced by activation by the upstream or preceding kinases. Moreover, measurement of SAPK inhibition is closely correlated with JNK inhibition.

Inhibitors of protein kinase catalytic activity are known in the art. See WO 98124432 (indoline compounds that inhibit FLK protein kinase); WO 97/45409 (substituted tetralylmethylene-oxindole analogues that inhibit tyrosine kinase). In particular, small molecule inhibitors typically block the binding of substrates by tightly interacting with the protein kinase ATP binding site (or "active site"). See WO 98/24432. It is desirable to identify small-molecule compounds that may be readily synthesized and are effective in inhibiting the catalytic activity of protein kinases, in particular of the JNK protein kinases.

Indolinone (also known as oxindole) compounds asserted to be useful in the regulating abnormal cell proliferation through tyrosine kinase inhibition are disclosed for example in WO 96/40116, WO 98/07695, WO 95/01349, WO 96/32380, WO 96/22976, WO 96/16964 and WO 98/50356 (2-indolinone derivatives as modulators of protein kinase activity); Mohammadi et. al, Science, Vol. 276, May 9, 1997, pp. 955–960. Oxindole derivatives have also been described for various other therapeutic uses: 5,206,261 (improvement of cerebral function); WO 92/07830 (peptide antagonists); EP 580 502 A1 (antioxidants).

There continues to be a need for easily synthesized, small molecule compounds effective in inhibiting JNK protein kinase and thus useful in the treatment or control of pathological proliferative conditions, for example inflammatory diseases and neuro-degenerafive diseases, in particular, rheumatoid arthritis. It is thus an object of this invention to provide such compounds and compositions containing such compounds.

SUMMARY OF THE INVENTION

The present invention relates to 4,5-pyrazinoxindoles capable of inhibiting the activity of one or more JNK protein kinases. Such compounds are useful for the treatment of inflammatory diseases and neuro-degenerative diseases. In particular, the compounds of the present invention are especially useful in the treatment or control of rheumatoid arthritis.

The compounds of the present invention are 4,5-pyrazinoxindoles having the following formula:

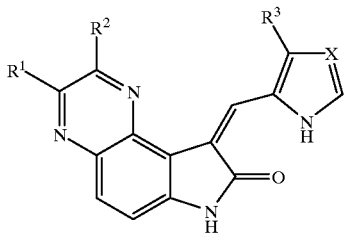

I and prodrugs and pharmaceutically active metabolites of compounds of Formula I; and the pharmaceutically acceptable salts of the foregoing compounds, wherein:

$R^1$ and $R^2$ are independently selected from the group consisting of
—H,
—$OR^4$,
—$COR^4$,
$COOR^4$,
—$CONR^5R^8$,
—$NR^5R^6$,
lower alkyl which optionally may be substituted by the group consisting of —$OR^4$, —$NR^5R^6$, halogen, —$COR^4$, —$COOR^4$, —$OCOR^4$, —$CONR^5R^6$, —$CN$, —$SO_2R^4$, —$SO_2NR^5R^6$, cycloalkyl, heterocycle, aryl, and heteroaryl, wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^4$, —$NR^5R^6$ halogen, —$COR^4$, —$COOR^4$, —$OCOR^4$, —$CONR^5R^6$, —$CN$, —$SO_2R^4$, —$SO_2NR^5R^6$, lower alkyl, heterocycle, aryl, and heteroaryl, wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^4$, —$NR^5R^6$, halogen, —$COR^4$, —$COOR^4$, —$OCOR^4$, —$CONR^5R^6$, —$CN$, —$SO_2R^4$, —$SO_2NR^5R^6$, lower alkyl, cycloalkyl, aryl, and heteroaryl, wherein the lower alkyl and cycloalkyl each may be optionally substituted by the group $R^{11}$ and the aryl and heteroaryl each may be optionally substituted by the group $R^{12}$,
aryl which optionally may be substituted by the group consisting of —$OR^4$, —$NR^5R^6$, halogen, —$NO_2$, perfluoroalkyl, —$COR^4$, —$COOR^4$, —$OCOR^4$, —$CONR^5R^6$, —$CN$, —$SO_2R^4$, —$SO_2NR^5R^6$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$,
heteroaryl which optionally may be substituted by the group consisting of —$OR^4$, —$NR^5R^6$, halogen, —$NO_2$, perfluoroalkyl, —$COR^4$, —$COOR^4$, —$OCOR^4$, —$CONR^5R^6$, —$CN$, —$SO_2R^4$, —$SO_2NR^5R^6$, lower alkyl, cycloalkyl, heterocycle, aryl, and heteroaryl and wherein the lower alkyl, cycloalkyl and heterocycle each may be optionally substituted by the group $R^{11}$ and the aryl and heteroaryl each may be optionally substituted by the group $R^{12}$, or alternatively, $R^1$ and $R^2$ optionally can form a ring having 5–7 atoms, aid ring optionally including one or more heteroatoms and being optionally ubstituted by the group consisting of —$OR^8$, —$COR^7$, —$COOR^7$, —$OCOR^4$, —$CONR^7R^9$, —$NR^8R^9$, and lower alkyl which optionally may be substituted by the group $R^{11}$.

$R^3$ is selected from the group consisting of
—H
—$OR^4$
—$COR^4$
—$COOR^4$
—$OCOR^4$
—$CONR^5R^6$
halogen
—$CN$
perfluoroalkyl
—$NR^5R^6$, and
lower alkyl which optionally may be substituted by —$OR^4$, —$OCOR^4$, or —$NR^5R^6$;

$R^4$ is selected from the group consisting of
—H,
lower alkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$,
aryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, cycloalkyl, lower alkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^5$ and $R^6$ are each independently selected from the group consisting of
—H,
—$COR^7$,
—$COOR^7$,
—$CONR^7R^9$, and lower alkyl which optionally may be substituted by the group consisting of —OR$^8$, —COOR$^7$, —COR$^7$, —CONR$^7$R$^8$, —NR$^7$R$^8$, —SO$_2$R$^7$, —SO$_2$NR$^7$R$^8$, cycloalkyl, heterocycle, aryl, and heteroaryl, and wherein the cycloalkyl and heterocycle each may be optionally substituted by the group R$^{11}$ and the aryl and heteroaryl each may be optionally substituted by the group R$^{12}$, cycloalkyl which optionally may be substituted by the group consisting of —OR$^8$, —COOR$^7$, —COR$^7$, —CONR$^7$R$^8$, —NR$^7$R$^8$, —SO$_2$R$^7$, —SO$_2$ NR$^7$R$^8$, lower alkyl, heterocycle, aryl, and heteroaryl, and wherein the lower alkyl and heterocycle each may be optionally substituted by the group R$^{11}$ and the aryl and heteroaryl each may be optionally substituted by the group R$^{12}$.

heterocycle which optionally may be substituted by the group consisting of —OR$^8$, —COOR$^7$, —COR$^7$, —CONR$^7$R$^8$, —NR$^7$R$^8$, —SO$_2$R$^7$, —SO$_2$NR$^7$R$^8$, cycloalkyl, lower alkyl, aryl, and heteroaryl, and wherein the cycloalkyl and lower alkyl each may be optionally substituted by the group R$^{11}$ and the aryl and heteroaryl each may be optionally substituted by the group R$^{12}$, aryl which optionally may be substituted by the group consisting of OR$^8$, —COOR$^7$, —COR$^7$, —CONR$^7$R$^8$, —NR$^7$R$^8$, —NO$_2$, halogen, perfluoroalkyl, —SO$_2$R$^7$, —SO$_2$NR$^7$R$^8$, lower alkyl, cycloalkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$, and heteroaryl which optionally may be substituted by the group consisting of —OR$^8$, —COOR$^7$, —COR$^7$, —CONR$^7$R$^8$, —NR$^7$R$^8$, —NO$_2$, halogen, perfluoroalkyl, —SO$_2$R$^7$, —SO$_2$NR$^7$R$^8$, lower alkyl, cycloalkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$; or alternatively, —NR$^5$R$^6$ can optionally form a ring having 3 to 7 atoms, said ring optionally including one or more additional hetero atoms and being optionally substituted by the group consisting of lower alkyl, —OR$^8$, —COR$^7$, —COOR$^7$, —CONR$^7$R$^9$, and —NR$^8$R$^9$;

R$^7$ is selected from the group consisting of
—H, and
lower alkyl which optionally may be substituted by the group consisting of cycloalkyl, heterocycle, aryl, heteroaryl, —OR$^9$, and —NR$^8$R$^9$;

R$^8$ is selected from the group consisting of
—H,
—COR$^9$
—CONR$^{10}$R$^9$, and
lower alkyl which optionally may be substituted by R$^{11}$;

R$^9$ and R$^{10}$ are each independently selected from the group consisting of —H and lower alkyl;

R$^{11}$ is selected from the group consisting of —OR$^9$, —COR$^9$, —COOR$^9$, —OCOR$^9$, —CONR$^9$R$^{10}$, —NR$^9$R$^{10}$, —N(COR$^9$)R$^{10}$, —SO$_2$R$^9$, —SO$_2$NR$^9$R$^{10}$;

R$^{12}$ is selected from the group consisting of —OR$^9$, —COR$^9$, —COOR$^9$, —OCOR$^9$, —CONR$^9$R$^{10}$, —NR$^9$R$^{10}$, —N(COR$^9$)R$^{10}$, —SO$_2$R$^9$, —SO$_2$NR$^9$R$^{10}$, halogen, —CN, —NO$_2$, perfluoroalkyl; and X is selected from the group consisting of —N— and —C—.

The present invention is further directed to pharmaceutical compositions comprising a pharmaceutically effective amount of any one or more of the above-described compounds and a pharmaceutically acceptable carrier or excipient.

The present invention is also directed to novel intermediates useful in the synthesis of the above described compounds.

The present invention is also directed to a method for treating solid tumors, in particular breast or colon tumors, by administering to a human patient in need of such therapy an effective amount of a compound of Formula I, its salts and/or prodrugs.

DETAILED DESCRIPTION OF THE INVENTION

Definitions

As used herein, the following terms shall have the following definitions.

"Aryl" means an aromatic group having 5 to 10 atoms and consisting of one or two rings. Examples of aryl groups include phenyl and 1- or 2-naphthyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective Amount" means an amount of at least one compound of Formula I, or a pharmaceutically acceptable salt, prodrug or metabolite thereof, that inhibits the development or proliferation of (1) an inflammatory disease or response and/or (2) a neuro-degenerative disease or response, such as for example, and not as a limitation, rheumatoid arthritis.

"Halogen" means fluorine, chlorine, bromine or iodine.

"Heteroaryl" groups are aromatic groups having 5 to 10 atoms, one or 2 rings, and containing one or more hetero atoms. Examples of heteroaryl groups are 2-, 3- or 4-pyridyl, tetrazolyl, oxadiazolyl, pyrazinyl, quinolyl, pyrrolyl, and imidazolyl.

"Hetero atom" means an atom selected from N, O and S.

"Heterocycle" means a 3- to 10-membered non-aromatic, partially or completely saturated hydrocarbon group, such as tetrahydroquinolyl, which contains one or two rings and at least one hetero atom.

"IC$_{50}$" refers to the concentration of a particular 4,5-pyrazinoxindole required to inhibit 50% of cJun phosphorylation, which is a measure of inhibition of SAPK activity. IC$_{50}$ can be measured, inter alia, using the assay described herein in Example 7, infra.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable salt" refers to conventional acid-addition salts or base-addition salts which retain the biological effectiveness and properties of the compounds of Formula I and are formed from suitable non-toxic organic or inorganic acids or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quarternary ammonium hydroxide, such as for example tetramethylammonium hydroxide.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of Formula I which is pharmaceutically acceptable and effective.

"Prodrug" refers to a compound that may be converted under physiological conditions or by solvolysis to any of the compounds of Formula I or to a pharmaceutically acceptable salt of a compound of Formula I. A prodrug may be inactive when administered to a subject but is converted in vivo to an active compound of Formula I.

"Substituted," as in for example "substituted alkyl," means that the substitution can occur at one or more positions and, unless otherwise indicated, that the substituents are independently selected from the specified options.

The Compounds

In one embodiment, the current invention is directed to compounds having the formula:

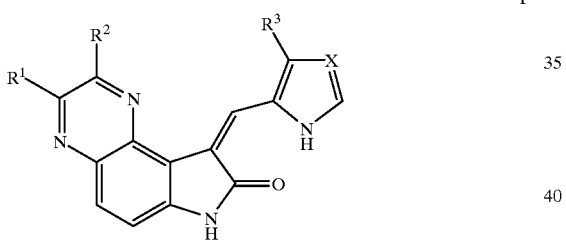

I and prodrugs and pharmaceutically active metabolites of compounds of Formula 1; and the pharmaceutically acceptable salts of the foregoing compounds, wherein:

$R^1$ and $R^2$ are independently selected from the group consisting of
—H,
—$COR^4$,
—$COOR^4$,
—$CONR^5R^6$,
—$NR^5R^6$,
lower alkyl which optionally may be substituted by the group consisting of —$OR^4$, —$NR^5R^6$, halogen, —$COR^4$, —$COOR^4$, —$OCOR^4$, -$CONR5R^6$, —CN, —$SO_2R^4$, —$SO_2NR^5R^6$, cycloalkyl, heterocycle, aryl, and heteroaryl, wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^4$, —$NR^5R^6$ halogen, —$COR^4$, —$COOR^4$, —$OCOR^4$, —$CONR^6R^6$, —CN, —$SO_2R^4{}_1$, —$SO_2NR^5R^6$, lower alkyl, heterocycle, aryl, and heteroaryl, wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^4$, —$NR^5R^6$, halogen, —$COR^4$, —$COOR^4$, —$OCOR^4$, —$CONR^5R^6$, —CN, -$SO_2R^4$, —$SO_2NR^5R^6$, lower alkyl, cycloalkyl, aryl, and heteroaryl, wherein the lower alkyl and cycloalkyl each may be optionally substituted by the group $R^{11}$ and the aryl and heteroaryl each may be optionally substituted by the group $R^{12}$,
aryl which optionally may be substituted by the group consisting of —$OR^4$, —$NR^5R^6$, halogen, —$NO_2$, perfluoroalkyl, —$COR^4$, —$COOR^4$, —$OCOR^4$, —$CONR^5R^6$, —CN, —$SO_2R^4$, —$SO_2NR^5R^6$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$,
heteroaryl which optionally may be substituted by the group consisting of —$OR^4$, —$NR^5R^6$, halogen, —$NO_2$, perfluoroalkyl, —$COR^4$, —$COOR^4$, —$OCOR^4$, —$CONR^5R^6$, —CN, —$SO_2R^4$, —$SO_2NR^5R^6$, lower alkyl, cycloalkyl, heterocycle, aryl, and heteroaryl and wherein the lower alkyl, cycloalkyl and heterocycle each may be optionally substituted by the group $R^{11}$ and the aryl and heteroaryl each may be optionally substituted by the group $R^{12}$, or
alternatively, $R^1$ and $R^2$ optionally can form a ring having 5–7 atoms, said ring optionally including one or more heteroatoms and being optionally substituted by the group consisting of —$OR^8$, —$COR^7$, —$COOR^7$, —$OCOR^4$, —$CONR^7R^9$, —$NR^8R^9$, and lower alkyl which optionally may be substituted by the group $R^{11}$.

$R^3$ is selected from the group consisting of
—$OR^4$
—CO $R^4$
—$COOR^4$
—$OCOR^4$
—$CONR^5R^6$
halogen
—CN
perfluoroalkyl
—$NR^5R^6$, and
lower alkyl which optionally may be substituted by —$OR^4$, —$OCOR^4$, or —$NR^5R^6$;

$R^4$ is selected from the group consisting of
—H,
lower alkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$,
cycloalkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$,
heterocycle which optionally may be substituted by the group consisting of —$OR^8$, —$COOR^7$, —$COR^7$, —CONR$^5$R$^6$, —NR$^5$R$^6$, —SO$_2$R$^7$, —SO$_2$NR$^5$R$^6$, cycloalkyl, lower alkyl, aryl, and heteroaryl, and wherein the cycloalkyl and lower alkyl each may be optionally substituted by the group R$^{11}$ and the aryl and heteroaryl each may be optionally substituted by the group R$^{12}$, aryl which optionally may be substituted by the group consisting of —OR$^8$, —COOR$^7$, —COR$^7$, —CONR$^5$R$^6$, —NR$^5$R$^6$, —NO$_2$, halogen, perfluoroalkyl, —SO$_2$R$^7$, —SO$_2$NR$^5$R$^6$, lower alkyl, cycloalkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$, and heteroaryl which optionally may be substituted by the group consisting of —OR$^8$, —COOR$^7$, —COR$^7$, —CONR$^5$R$^6$, —NR$^5$R$^6$, —NO$_2$, halogen, perfluoroalkyl, —SO$_2$R$^7$, —SO$_2$NR$^5$R$^6$, cycloalkyl, lower alkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$;

R$^5$ and R$^6$ are each independently selected from the group consisting of
—H,
—COR$^7$,
—COOR$^7$,
—CONR$^7$R$^9$, and
lower alkyl which optionally may be substituted by the group consisting of —OR$^8$, —COOR$^7$, —COR$^7$, —CONR$^7$R$^8$, —NR$^7$R$^8$, —SO$_2$R$^7$, —SO$_2$NR$^7$R$^8$, cycloalkyl, heterocycle, aryl, and heteroaryl, and wherein the cycloalkyl and heterocycle each may be optionally substituted by the group R$^{11}$ and the aryl and heteroaryl each may be optionally substituted by the group R$^{12}$, cycloalkyl which optionally may be substituted by the group consisting of —OR$^8$, —COOR$^7$, —COR$^7$, —CONFR$^7$R$^8$, —NR$^7$R$^8$, —SO$_2$R$^7$, —SO$_2$NR$^7$R$^8$, lower alkyl, heterocycle, aryl, and heteroaryl, and wherein the lower alkyl and heterocycle each may be optionally substituted by the group R$^1$l and the aryl and heteroaryl each may be optionally substituted by the group R$^{12}$, heterocycle which optionally may be substituted by the group consisting of —OR$^8$, —COOR$^7$, —COR$^7$, —CONR$^7$R$^8$, —NR$^7$R$^8$, —SO$_2$R$^7$, —SO$_2$NR$^7$R$^8$, cycloalkyl, lower alkyl, aryl, and heteroaryl, and wherein the cycloalkyl and lower alkyl each may be optionally substituted by the group R$^{11}$ and the aryl and heteroaryl each may be optionally substituted by the group R$^{12}$, aryl which optionally may be substituted by the group consisting of OR$^8$, —COOR$^7$, —COR$^7$, —CONR$^7$R$^8$, —NR$^7$R$^8$, —NO$_2$, halogen, perfluoroalkyl, —SO$_2$R$^7$, —SO$_2$NR$^7$R$^8$, lower alkyl, cycloalkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$, and heteroaryl which optionally may be substituted by the group consisting of —OR$^8$, —COOR$^7$, —COR$^7$, —CONR$^7$R$^8$, —NR$^7$R$^8$, —NO$_2$, halogen, perfluoroalkyl, —SO$_2$R$^7$, —SO$_2$NR$^7$R$^8$, lower alkyl, cycloalkyl, heterocycle, aryl, and heteroaryl, and wherein the lower alkyl, cycloalkyl and heterocycle each may be optionally substituted by the group R$^{11}$ and the aryl and heteroaryl each may be optionally substituted by the group R$^{12}$; or alternatively, —NR$^5$R$^6$ can optionally form a ring having 3 to 7 atoms, said ring optionally including one or more additional hetero atoms and being optionally substituted by the group consisting of lower alkyl, —OR$^8$, —COR$^7$, —COOR$^7$, —CONR$^7$R$^9$, and —NR$^8$R$^9$;

R$^7$ is selected from the group consisting of
—H, and
lower alkyl which optionally may be substituted by the group consisting of cycloalkyl, heterocycle, aryl, heteroaryl, —OR$^9$, and —NR$^8$R$^9$;

R$^8$ is selected from the group consisting of
—H,
—COR$^9$
—CONR$^{10}$R$^9$, and
lower alkyl which optionally may be substituted by R$^{11}$;

R$^9$ and R$^{10}$ are each independently selected from the group consisting of —H and lower alkyl;

R$^{11}$ is selected from the group consisting of —OR$^9$, —COR$^9$, —COOR$^9$, —OCOR$^9$, —CONR$^9$R$^{10}$, —NR$^9$R$^{10}$, —N(COR$^9$R$^{10}$, —SO$_2$R$^9$, —SO$_2$NR$^9$R$^{10}$;

R$^{12}$ is selected from the group consisting of —OR$^9$, —COR$^9$, —COOR$^9$, —OCOR$^9$, —CONR$^9$R$^{10}$, —NR$^9$R$^{10}$, —N(COR$^9$)R$^{10}$, —SO$_2$R$^9$, —SO$_2$R$^9$R$^{10}$, halogen, —CN, —NO$_2$, perfluoroalkyl; and X is selected from the group consisting of —N— and —C—.

Preferred perfluoroalkyls according to the present invention include —CF$_3$.

In a preferred embodiment of the compounds of Formula I, R$^1$ and R$^2$ are independently selected from the group consisting of
—H,
—NR$^5$R$^6$,
lower alkyl which optionally may be substituted by R$^{11}$, cycloalkyl, heterocycle, aryl and heteroaryl, wherein the cycloalkyl and heterocycle optionally may be substituted by R$^{11}$, and the aryl and heteroaryl optionally may be substituted by R$^{12}$;

cycloalkyl which optionally may be substituted by R$^{11}$, lower alkyl, heterocycle, aryl and heteroaryl, wherein the lower alkyl and heterocycle optionally may be substituted by R$^{11}$, and the aryl and heteroaryl optionally may be substituted by R$^{12}$;

heterocycle which optionally may be substituted by R$^{11}$, lower alkyl, cycloalkyl, aryl and heteroaryl, wherein the lower alkyl and cycloalkyl optionally may be substituted by R$^{11}$, and the aryl and heteroaryl optionally may be substituted by R$^{12}$;

aryl which optionally may be substituted by R$^{12}$, lower alkyl, cycloalkyl, heterocycle, aryl, and heteroaryl, wherein the lower alkyl, heterocycle and cycloalkyl optionally may be substituted by R$^{11}$, and the aryl and heteroaryl optionally may be substituted by R$^{12}$;

heteroaryl which optionally may be substituted by R$^{12}$, lower alkyl, cycloalkyl, heterocycle, aryl, and heteroaryl, wherein the lower alkyl, cycloalkyl and heterocycle optionally may be substituted by R$^{11}$, and the aryl and heteroaryl optionally may be substituted by R$^{12}$; or alternatively, $R^1$ and $R^2$ may form a ring having 5 to 7 atoms and optionally being substituted by the group consisting of —$OR^8$, —$COR^7$, —$COOR^7$, —$CONR^7R^9$, —$NR^8R^9$, and lower alkyl which optionally may be substituted by $R^{11}$.

In another preferred embodiment of the compounds of Formula I, $R^3$ is selected from the group consisting of
—H,
—$OR^4$,
—$NR^5R^6$,
lower alkyl which optionally may be substituted by the group consisting of —$OR^4$ and —$NR^5R^6$.

In another preferred embodiment of the compounds of Formula I, $R^3$ is selected from the group consisting of
—H,
—$OR^9$, and
lower alkyl which optionally may be substituted by the group consisting of —$OR^9$ and —$NR^9R^{10}$.

The following are examples of preferred compounds of Formula I:

(Z)-7,9-Dihydro-2,3-dimethyl-9-[(3-methoxy-1H-pyrrol-2-yl)methylene]-8H-pyrrolo-[3,2-f]quinoxalin-8-one (A), (Z)-3-Butyl-7,9-dihydro9-[(3-methoxy-1H-pyrrol-2-yl) methylene]-2-methyl-8H-pyrrolo[3,2-f]quinoxalin-8-one and (Z)-2-butyl-7,9-dihydro-9-[(3-methoxy-1H-pyrrol-2-yl)methylene]-3-methyl-8H-pyrrolo[3,2-f] quinoxalin-8-one (B), (Z)-7,9-Dihydro-9-[(3-methoxy-1H-pyrrol-2-yl) methylene]-2-methyl-3-phenyl-8H-pyrrolo[3,2-f] quinoxalin-8-one and (Z)-7,9-dihydro-9-[(3-methoxy-1H-pyrrol-2-yl)methylene]-3-methyl-2-phenyl-8H-pyrrolo[3,2-f]quinoxalin-8-one (C), (Z)-7,9-Dihydro-2,3-di-(2-furanyl)-9-[(3-methoxy-1H-pyrrol-2-yl)methylene]-8H-pyrrolo[3,2-f]quinoxalin-8-one (D), (Z)-1,3,5,6,7,8-Hexahydro-3-[(3-methoxy-1 H-pyrrol-2-yl)methylene]-2H-pyrrolo[3,2-a]phenazin-2-one (E).

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds of Formula I

The compounds of Formula I may be prepared by processes known in the art. Suitable processes for synthesizing these compounds are provided in the examples below. Generally, these compounds may be prepared according to the following synthesis scheme:

Step A

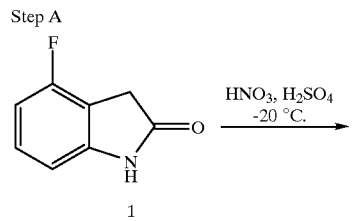

Step B

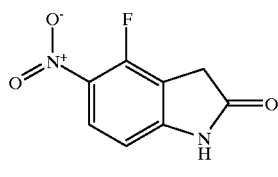

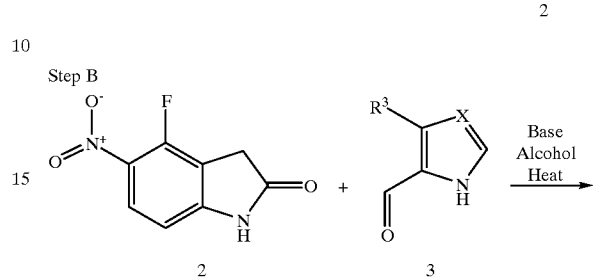

Step C

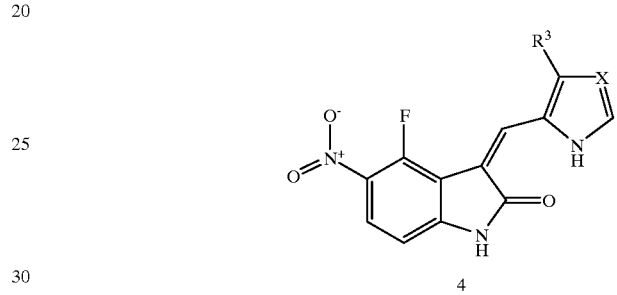

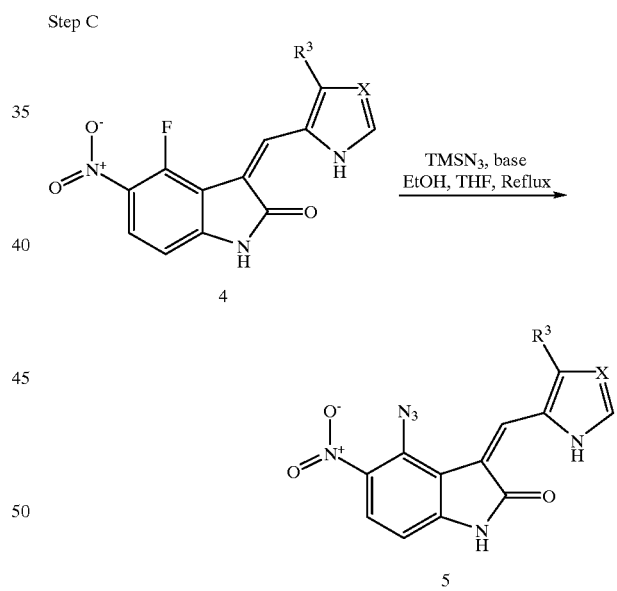

Step D

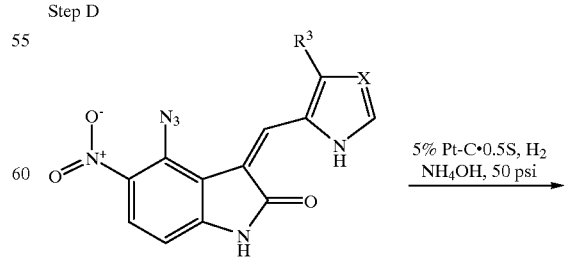

-continued

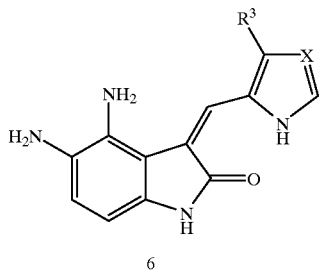

5

Step E

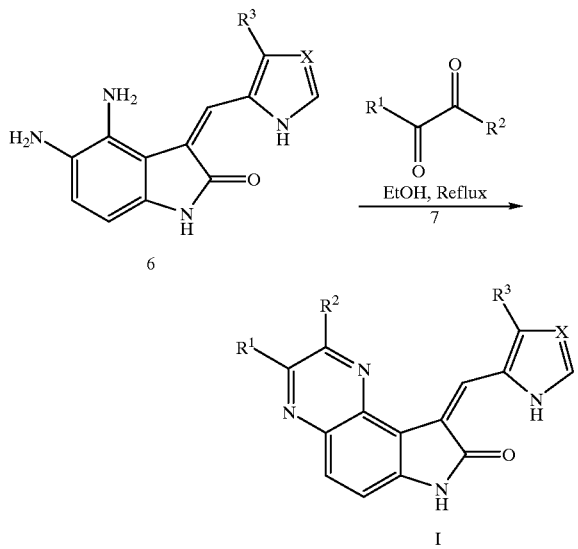

Compositions/Formulations

In an alternative embodiment, the present invention is directed to pharmaceutical compositions comprising at least one compound of Formula I or a prodrug thereof, or a pharmaceutically acceptable salt of a compound of Formula I or a prodrug of such compound.

These pharmaceutical compositions can be administered orally, for example, in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of Formula I, prodrugs of such compounds, or the salts thereof, may be manufactured in a manner that is know in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid poll. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of Formula I.

Dosages

As mentioned above, the compounds of Formula 1, prodrugs thereof, and their salts, and compositions containing these compounds are useful in the treatment or control of inflammatory diseases and neuro-degenerative diseases, in particular, in the treatment or control of rheumatoid arthritis.

A therapeutically effective amount of a compound in accordance with this invention means an amount of compound that is effective to prevent, alleviate or ameliorate symptoms of disease. Determination of a therapeutically effective amount is within the skill in the art.

The therapeutically effective amount or dosage of a compound of Formula I can vary within wide limits and will be adjusted to the individual requirements in each particular case. In general, in the case of oral or parenteral administration to adult humans weighing approximately 70 Kg, a daily dosage of about 10 mg to about 10,000 mg. preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as for example the general scheme provided above. The following examples illustrate preferred methods for synthesizing the compounds and formulations of the present invention.

Example 1

General Synthesis Methods and Starting Materials

General Method

Preparation of (Z)-7,9-Dihydro-9-[(3-methoxy-1H-pyrrol-2-yl)methylene]-8H-pyrrolo[3,2-f]quinoxalin-8-ones

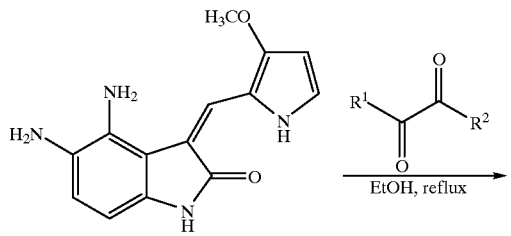

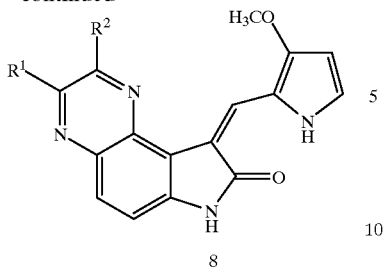

8

Starting Material 2
1,3-Dihydro-4-fluoro-5-nitro-2H-indol-2-one

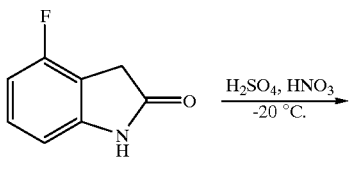

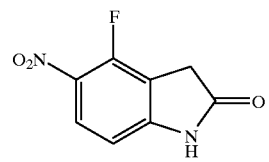

To a suspension of the starting diamino derivative (60 mg, 0.22 mmol) (Starting Material 5) in EtOH (3 mL) was added 10 eq of diketone. Upon heating, the suspension was converted to a heavier orange solid. The mixture is cooled to r.t. and the precipitate was collected by suction filtration, then dried overnight in a vacuum oven. Unsymmetrical diketones afforded a mixture of regioisomers.

Starting Material 1

1,3-Dihydro-4-fluoro-2H-indol-2-one

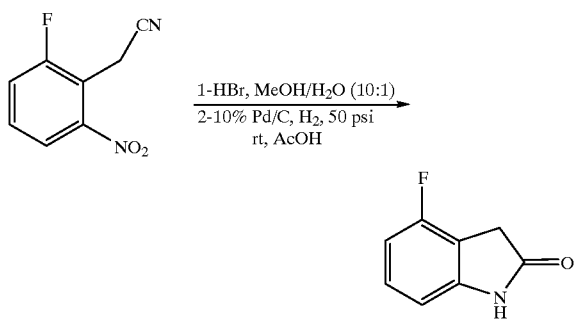

6-Fluoro-2-nitrobenzyl cyanide (23.10 g, 0.12 mole) (prepared according to A. Kalir et. al., *Synthesis*, 1987, 514–515) was dissolved in 10:1 MeOH/H$_2$O (250 mL) and the solution was chilled in an ice water bath. HBr gas was bubbled into the cold mixture for 75 min. The solution was allowed to warm up to r.t. and then concentrated to half its volume under reduced pressure. THF (100 mL), water (100 mL) and conc. HCl (6 mL) were successively added at r.t. and stirring was maintained for 75 min. The mixture was poured into water and extracted with ethyl acetate. The combined organic layers were washed with water, sat. aq. NaHCO$_3$ and brine, then dried over sodium sulfate and concentrated under reduced pressure. This material (20.9 g) was dissolved in acetic acid (200 mL) and hydrogenated for 2 h in a Parr apparatus at 50 Psi, in the presence of 10% Pd/C (4.33 g). The reaction mixture was filtered through a cake of Celite® (Fisher Scientific), and the cake was washed with acetic acid. The solution was concentrated under reduced pressure and dissolved in MeOH (300 mL) containing 1N NaOH (15 mL). This mixture was poured into 2:1 sat aq. NaCl/H$_2$O (600 mL) and extracted with ethyl acetate. The combined organic layers were washed with brine, dried over sodium sulfate and concentrated. The crude residue was triturated with ether to yield 5.8 g (first crop) of pure 1,3-dihydro4-fluoro-2H-indol-2-one. The mother liquor was chromatographed on Silica Gel (230–400 mesh, eluted with 40% ethyl acetate in hexane) to yield an additional 1.6 g of product (overall yield from cyanide: 41%).

1,3-Dihydro4-fluoro-2H-indol-2-one (6.29g, 41.6 mmol) (Starting Material 1 above) was dissolved in 100 mL conc. H$_2$SO$_4$ with stirring. This mixture was cooled in a dry ice-acetone bath to –20° C. to which was added slowly over 30 min. a solution of 2.6 mL (41.6 mmol) HNO$_3$ in 10 mL H$_2$SO$_4$. Thereafter the reaction mixture was stirred at –20° C. for 45 min. (TLC: 50% ethyl acetate in hexane showed complete reaction after 30 min.), then poured into 1 L ice and water, extracted with 2×200 mL ethyl acetate, washed with 2×200 mL sat. NaCl solution, dried over Na$_2$SO$_4$, filtered and concentrated at 45° C. under high vacuum to give a brown solid (7.87 g). This material was recrystallized from ethyl acetate to afford 3.94 g (first crop only) of pure product. The mother liquor was chromatographed on Silica Gel (230–400 mesh, eluted with 50% ethyl acetate in hexane) to give 1.91 g of additional material. (Total yield: 5.85 g, 71.7%).

Starting Material 3

(Z)-1,3-Dihydro-4-fluoro-3-[(3-methoxy-1H-pyrrol-2-yl)methylone]-5-nitro-2H-indol-2-one

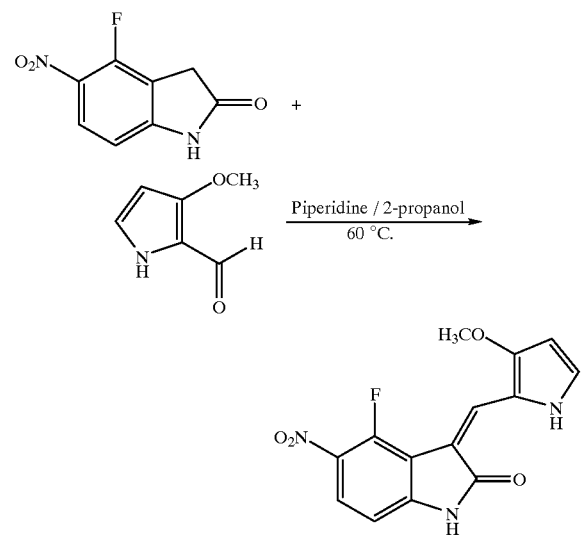

1,3-Dihydro-4-fluoro-5-nitro-2H-indol-2-one (5.25 g, 26.8 mmol) (Starting Material 2) was suspended in 110 mL solution of 1–35% piperidine (Aldrich) in 2-propanol (Fisher). 3-Methoxy-2-pyrrole carboxaldehyde (3.68 g, 29.4 mmol, 1.1 eq.) (prepared according to F. Bellamy et. al., *J. Chem. Research* (S) 1979, 18–19; *J. Chem. Research* (M), 1979, 0101–0116) was added and this mixture heated at 60°

C. for 3.5 hours (TLC: 50% ethyl acetate in hexane). The reaction mixture was poured into 1 L ice and water mixture and the solid precipitate filtered, washed with water and dried at 50° C. under high vacuum to give the product as an orange-brown solid. (Yield 6.6 g, 81%).

Starting Material 4

(Z)-4-Azido-1,3-dihydro-3-[(3-methoxy-1H-pyrrol-2-yl) methylene]-5-nitro-2H-indol-2-one

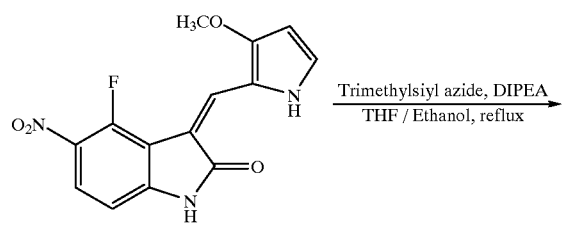

(Z)-1,3-Dihydro4-fluoro-3-[(3-methoxy-1H-pyrrol-2-yl) methylene]-5-nitro-2H-indol-2-one (6.60 g, 21.8 mmol) (Starting Material 3 above) was suspended in 330 mL of THF and 165 mL of ethanol. To this mixture was added diisopropylethylamine (56.9 ml, 326 mmol) (Aldrich) and trimethylsilyl azide (28.6 mL, 218 mmol) (Aldrich). The reaction mixture was heated at reflux overnight, and then poured into 2 L mixture of ice and 1 N HCl solution. The solid precipitate was filtered, washed with water and dried at 50° C. under high vacuum to give (Z)4-azido-1,3-dihydro-3-[(3-methoxy-1H-pyrrol-2-yl)methylene]-5-nitro-2H-indol-2-one as a dark red solid. (Yield 6.44 g, 90%)

Startng Material (Z)-4,5-Diamino-1,3-dihydro-3-[(3-methoxy-1H-pyrrol-2-yl) methylene]-2H-indol-2one

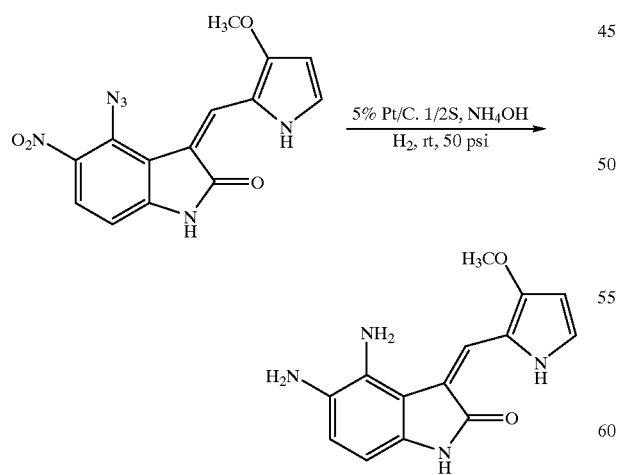

(Z)-4-Azido-1,3-dihydro-3-[(3-methoxy-1H-pyrrol-2-yl) methylene]-5-nitro-2H-indol-2-indol-2-one (2.08 g, 6.37 mmol) (Starting Material 4 above) was dissolved in THF (160 mL) at r.t. Ammonium hydroxide was added (2 mL), followed by a catalytic amount of poisoned platinum on carbon (5% Pt/C-1/2S, 300 mg) (Engelhard Ind.). The reaction mixture was hydrogenated in a Parr bomb under 50 psi of hydrogen for 12 h. The mixture was filtered through a cake of Celite®, the cake was washed twice with THF, and the filtrate was concentrated under reduced pressure. The crude material was purified by flash chromatography on Silica Gel (230–400 mesh, eluted with 75% ethyl acetate in hexane) to yield (Z)-4,5-diamino-1,3-dihydro-3-[(3-methoxy-1 H-pyrrol-2-yl)methylene]-2H-indol-2-one (Yield 1.44 g, 84%).

Example 2

(Z)-7,9-Dihydro-2,3-dimethyl-9-[(3-methoxy-1H-pyrrol-2-yl)methylene]-8H-pyrrolo-[3,2-f] quinoxalin-8-one (A)

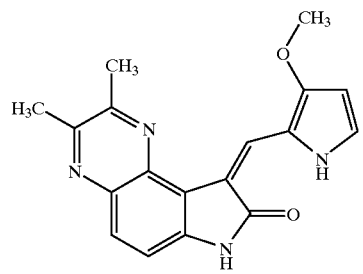

Using Method A above, (Z)-4,5-diamino-1,3-dihydro-3-[(3-methoxy-1H-pyrrol-2-yl)methylene]-2H-indol-2-one (60 mg, 0.22 mmol) (Starting Material 5) was condensed with 2,3-butanedione (135 μL) (Aldrich) in ethanol (3 ml) at reflux to give (Z)-7,9-dihydro-2,3-dimethyl-9-[(3-methoxy-1H-pyrrol-2-yl)methylene]-8H-pyrrolo-[3,2-f]quinoxalin-8-one in 100% yield.

Example 3

Mixture of (Z)-3-butyl-7,9-dihydro-9-[(3-methoxy-1H-pyrrol-2-yl)methylene]-2-methyl-8H-pyrrolo[3, 2-f]quinoxalin-8-one and (Z)-2-butyl-7,9-dihydro-9-[(3-methoxy-1H-pyrrol-2-yl)methylene]-3-methyl-8H-pyrrolo[3,2-f]quinoxalin-8-one (B)

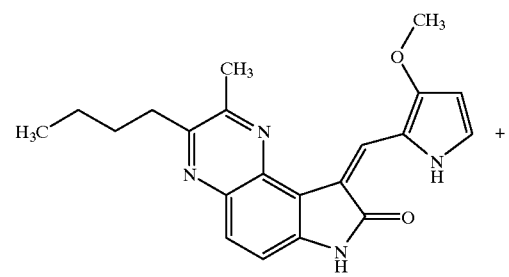

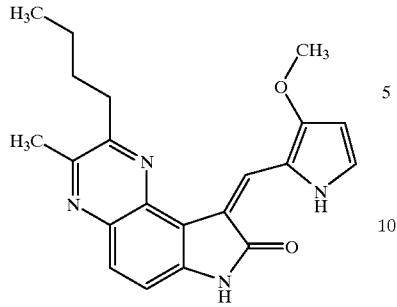

Using Method A above, (Z)4,5-diamino-1,3-dihydro-3-[(3-methoxy-1H-pyrrol-2-yl)methylene]-2H-indol-2-one (60 mg, 0.22 mmol) (Starting Material 5) was condensed with 2,3-heptanedione (282 μL) (Lancaster) in ethanol (3 mL) at reflux to give mixture of (Z)-3-butyl-7,9-dihydro-9-[(3-methoxy-1H-pyrrol-2-yl)methylene]-2-methyl-8H-pyrrolo[3,2-f]quinoxalin-8-one and (Z)-2-butyl-7,9-dihydro-9-[(3-methoxy-1H-pyrrol-2-yl)methylene]-3methyl-8H-pyrrolo[3,2-f]quinoxalin-8-one in 88% yield.

Example 4

Mixture of (Z)-7,9dihydro-9-[(3-methoxy-1H-pyrrol-2-yl)methylene]-2-methyl-3-phenyl-8H-pyrrolo[3,2-f]quinoxalin-8-one and (Z)-7,9-dihydro-9-[(3-methoxy-1H-pyrrol-2-yl)methylene]-methyl-2-phenyl-8H-pyrrolo[3,2-f]quinoxalin-8-one (C)

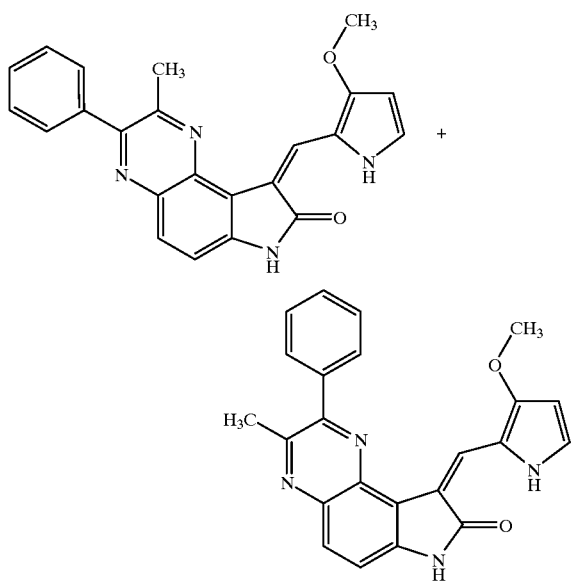

Using Method A above, (Z)-4,5-diamino-1,3-dihydro-3-[(3-methoxy-1H-pyrrol-2-yl)methylene]-2H-indol-2-one (60 mg, 0.22 mmol) (Starting Material 5) was condensed with 1-phenyl1,2-propanedione (326 μL) (Aldrich) in ethanol (3 mL) at reflux to give mixture of (Z)-7,9-dihydro-9-[(3-methoxy-1H-pyrrol-2-yl)methylene]-2-methyl-3-phenyl-8H-pyrrolo[3,2-f]quinoxalin-8-one and (Z)-7,9-dihydro-9-[(3-methoxy-1H-pyrrol-2-yl)-methylene-3-methyl-2-phenyl-8H-pyrrolo[3,2-f]quinoxalin-8-one in 46% yield.

Example 5

(Z)-7,9-Dihydro-2,3-di-(2-furanyl)-9-[(3-methoxy-1H-pyrrol-2-yl)methylene]-8H-pyrrolo[3,2-f]quinoxalin-8one (D)

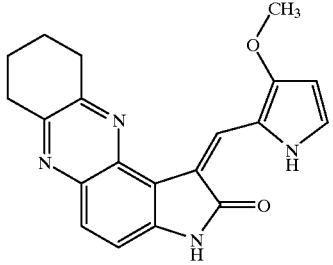

Using Method A above, (Z)-4,5-diamino-1,3-dihydro-3-[(3-methoxy-1H-pyrrol-2-yl)methylene]-2H-indol-2-one (60 mg, 0.22 mmol) (Starting Material 5) was condensed with furil (200 mg) (Aldrich) in ethanol (3 mL) at reflux to give (Z)-7,9-dihydro-2,3-di-(2-furanyl)-9-[(3-methoxy-1H-pyrrol-2-yl)methylene]-8H-pyrrolo[3,2-f]quinoxalin-8-one in 86% yield.

Example 6

(Z)-1,3,5,6,7,8-Hexahydro-3-[(3-methoxy-1H-pyrrol-2-yl)methylene]-2H-pyrrolo[3,2-a]phenazin-2-one (E)

Using Method A above, (Z)-4,5-diamino-1,3-dihydro-3-[(3-methoxy-1 H-pyrrol-2-yl)methylene]-2H-indol-2one (60 mg, 0.22 mmol) (Starting Material 5) was condensed with 1,2-cyclohexanedione (248 mg) (Aldrich) in ethanol (3 mL) at reflux to give (Z)-1,3,5,6,7,8-hexahydro-3-[(3-methoxy-1H-pyrrol-2-yl)methylene]-2H-pyrrolo[3,2-a]phenazin-2-one in 18% yield.

Example 7

SAPK Inhibitory Activity

The SAPK inhibitory activity of the compounds of the invention is demonstrated below. These effects indicate that the compounds of the present invention are useful in treating inflammatory diseases such as, for example, rheumatoid arthritis.

SAPK FlashPlate Assay

Human JNK is highly homologous to rat SAPK. To measure the inhibitory activity of test compounds, the compounds were tested in the rat SAPK assay. For the SAPK assay, purified GST-cJun (a chimeric protein containing cJun, a natural substrate of JNK) was coated on 96 well FlashPlates (New England Nuclear, Boston, Mass.). Purified rat SAPK (isoform β, Kyriakis et al. supra) was preincubated with preparations containing MEKK-1 and MKK4 for 30 minutes at 37° C. in assay buffer containing 25 mM HEPES, pH 7.5, 150 mM NaCl, 20 mM $MgCl_2$, 2 mM DTT, 0.001% Tween 20, 1 μM ATP freshly added. In the preincubation step, MEKK-1 phosphorylates and activates MKK-4, which in turn phosphorylates and activates SAPK. The activated SAPK was then added to the cJun coated FlashPlates along with $^{33}$P-ATP (0.32 μCi per reaction) and test compounds. The plates were incubated for 30 minutes at 37° C., then washed with PBS, 0.01% Tween 20, and counted in the Topcount scintillation counter (Packard Instrument Co., Downers Grove, Ill.). Dilutions of compounds were tested in duplicate in each assay. The percent inhibition of cJun phosphorylation (a measure of inhibition of SAPK activity) was determined by the following formula:

$$100 \times \left[ \frac{1 - \text{test compound} - \text{nonspecific}}{\text{total} - \text{nonspecific}} \right]$$

where "test compound" refers to the average counts per minute of the test duplicates, "nonspecific" refers to the average counts per minute when no SAPK was added, and "total" refers to the average counts per minute when no compound was added.

The results of the SAPK assay with various test compounds is summarized below in Table I.

TABLE I

| Compound | SAPK | |
|---|---|---|
| | % Inhibition | Concentration (μM) |
| A | ≧50% | <0.1 |
| B | ≧50% | 0.5 |
| C | ≧50% | 0.5 |
| D | ≧50% | 0.5 |
| E | ≧50% | <0.1 |

Example 8

Tablet Formulation

| Item | Ingredients | mg/Tablet | | | | | |
|---|---|---|---|---|---|---|---|
| 1 | Compound 1* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound 1 represents a compound of the invention.

Manufacturing Procedure

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 9

Capsule Formulation

| Item | Ingredients | mg/Capsule | | | | |
|---|---|---|---|---|---|---|
| 1 | Compound 1 * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

* Compound 1 represents a compound of the invention.

Manufacturing Procedure

1. Mix Items 1, 2 and 3 in a suitable mixer for 15 minutes.
2. Add Items 4 & 5 and mix for 3 minutes.
3. Fill into a suitable capsule.

Example 10

Injection Solution/Emulsion Preparation

| Item | Ingredient | mg/mL |
|---|---|---|
| 1 | Compound 1 * | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

* Compound 1 represents a compound of the invention.

Manufacturing Procedure

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

Example 11

Injection Solution/Emulsion Preparation

| Item | Ingredient | mg/mL |
|---|---|---|
| 1 | Compound 1 * | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

* Compound 1 represents a compound of the invention.
Manufacturing Procedure:
1. Dissolve item 1 in item 2
2. Add items 3, 4 and 5 to item 6 and mix until dispersed then homogenize.
3. Add the solution from step 1 to the mixture from step 2 and homogenize until the dispersion is translucent.
4. Sterile filter through a 0.2 um filter and fill into vials.

Manufacturing Procedure

1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.

What is claimed is:

1. A compound of formula

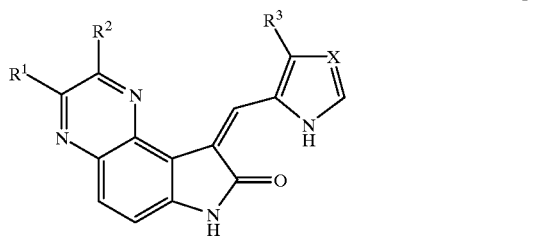

I or the pharmaceutically acceptable salts of the foregoing compounds, wherein:

$R^1$ and $R^2$ are independently selected from the group consisting of
—H,
—$NR^5R^6$,
lower alkyl which optionally may be substituted by —$OR^4$, —$COR^4$, —$COOR^4$, —$OCOR^4$, —$CONR^5R^6$, —$NR^5R^6$, —$SO_2R^4$, —$SO_2NR^5R^6$, cycloalkyl, heterocycle, aryl and heteroaryl, wherein the cycloalkyl and heterocycle optionally may be substituted by $R^{11}$, and the aryl and heteroaryl optionally may be substituted by $R^{12}$;
cycloalkyl which optionally may be substituted by —$OR^4$, —$COR^4$, —$COOR^4$, —$OCOR^4$, —$CONR^5R^6$, —$NR^5R^6$, —$SO_2R^4$, —$SO_2NR^5R^6$, lower alkyl, heterocycle, aryl and heteroaryl, wherein the lower alkyl and heterocycle optionally may be substituted by $R^{11}$, and the aryl and heteroaryl optionally may be substituted by $R^{12}$;
heterocycle which optionally may be substituted by —$OR^4$, —$COR^4$, —$COOR^4$, —$OCOR^4$, —$CONR^5R^6$, —$NR^5R^6$, —$SO_2R^4$, —$SO_2NR^5R^6$, lower alkyl, cycloalkyl, aryl and heteroaryl, wherein the lower alkyl and cycloalkyl optionally may be substituted by $R^{11}$, and the aryl and heteroaryl optionally may be substituted by $R^{12}$;
aryl which optionally may be substituted by —$OR^4$, —$NR^5R^6$, halogen, —$NO_2$, perfluoroalkyl, —$COR^4$, —$COOR^4$, —$OCOR^4$, —$CONR^5R^6$, —$CN$, —$SO_2R^4$, —$SO_2NR^5R^6$, lower alkyl, cycloalkyl, heterocycle, aryl and heteroaryl, wherein the lower alkyl, cycloalkyl and hetercycle optionally may be substituted by $R^{11}$, and the aryl and heteroaryl optionally may be substituted by $R^{12}$; and
heteroaryl which optionally may be substituted by —$OR^4$, —$NR^5R^6$, halogen, —$NO_2$, perfluoroalkyl, —$COR^4$, —$COOR^4$, —$OCOR^4$, —$CONR^5R^6$, —$CN$, —$SO_2R^4$, —$SO_2NR^5R^6$, lower alkyl, cycloalkyl, heterocycle, and aryl, wherein the lower alkyl, cycloalkyl and heterocycle optionally may be substituted by $R^{11}$, and the aryl optionally may be substituted by $R^{12}$; or
alternatively, $R^1$ and $R^2$ may form a ring having 5 to 7 atoms and optionally being substituted by the group consisting of —$OR^8$, —$COR^7$, —$COOR^7$, —$CONR^7R^9$, —$NR^8R^9$, and lower alkyl which optionally may be substituted by $R^{11}$.

$R^3$ is selected from the group consisting of
—H
—$OR^4$
—$COR^4$
—$COOR^4$
—$OCOR^4$
—$CONR^5R^6$
halogen
—$CN$
perfluoroalkyl
—$NR^5R^6$, and
lower alkyl which optionally may be substituted by —$OR^4$, —$OCOR^4$, or —$NR^5R^6$;

$R^4$ is selected from the group consisting of
—H,
lower alkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, lower alkyl, heterocycle, aryl, and heteroaryl, and wherein the lower alkyl and heterocycle each may be optionally substituted by the group $R^{11}$ and the aryl and heteroaxyl each may be optionally substituted by the group $R^{12}$,
heterocycle which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$,
aryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, lower alkyl, cycloallyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and
heteroaryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, cycloalkyl, lower alkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^5$ and $R^6$ are each independently selected from the group consisting of
—H,
—$COR^7$,
—$COOR^7$,
—$CONR^7R^9$, and
lower alkyl which optionally may be substituted by the group consisting of —$OR^8$, —$COOR^7$, —$COR^7$, —CONR⁷R⁸, —NR⁷R⁸, —SO₂NR⁷, —SO₂NR⁷R⁸, cycloalkyl, heterocycle, aryl, and heteroaryl, and wherein the cycloalkyl and heterocycle each may be optionally substituted by the group R¹¹ and the aryl and heteroaryl each may be optionally substituted by the group R¹², cycloalkyl which optionally may be substituted by the group consisting of —OR⁸, —COOR⁷, —COR⁷, —CONR⁷R⁸, —NR⁷R⁸, —SO₂R⁷, —SO₂NR⁷R⁸, lower alkyl, heterocycle, aryl, and heteroaryl, and wherein the lower alkyl and heterocycle each may be optionally substituted by the group R¹¹ and the aryl and heteroaryl each may be optionally substituted by the group R¹², heterocycle which optionally may be substituted by the group consisting of —OR⁸, —COOR⁷, —COR⁷, —CONR⁷R⁸, —NR⁷R⁸, —SO₂R⁷, —SO₂NR⁷R⁸, cycloalkyl, lower alkyl, aryl, and heteroaryl, and wherein the cycloalkyl and lower alkyl each may be optionally substituted by the group R¹¹ and the aryl and heteroaryl each may be optionally substituted by the group R¹², aryl which optionally may be substituted by the group consisting of OR⁸, —COOR⁷, —COR⁷, —CONR⁷R⁸, —NR⁷R⁸, —NO₂, halogen, perfluoroalkyl, —SO₂R⁷, —SO₂NR⁷R⁸, lower alkyl, cycloalkyl, heterocycle, aryl, and heteroaryl, and wherein the lower alkyl, cycloalkyl and heterocycle each may be optionally substituted by the group R¹¹ and the aryl and heteroaryl each may be optionally substituted by the group R¹², and heteroaryl which optionally may be substituted by the group consisting of —OR⁸, —COOR⁷, —COR⁷, —CONR⁷R⁸, —NR⁷R⁸, —NO₂, halogen, perfluoroalkyl, —SO₂R⁷, —SO₂NR⁷R⁸, lower alky, cycloalkyl, heterocycle, aryl, and heteroaryl, and wherein the lower alkyl, cycloalkyl and heterocycle each may be optionally substituted by the group R¹¹ and the aryl and heteroaryl each may be optionally substituted by the group R¹²; or alternatively, —NR⁵R⁶ can optionally form a ring having 3 to 7 atoms, said ring optionally including one or more additional hetero atoms and being optionally substituted by the group consisting of lower alkyl, —OR⁸, —COR⁷, —COOR⁷, —CONR⁷R⁹, and —NR⁸R⁹;

R⁷ is selected from the group consisting of
—H, and
lower alkyl which optionally may be substituted by the group consisting of cycloalkyl, heterocycle, aryl, heteroaryl, —OR⁹, and —NR⁸R⁹;

R⁸ is selected from the group consisting of
—H,
—COR⁹,
—CONR¹⁰R⁹, and
lower alkyl which optionally may be substituted by R¹¹;

R⁹ and R¹⁰ are each independently selected from the group consisting of —H and lower alkyl;

R¹¹ is selected from the group consisting of —OR⁹, —COR⁹, —COOR⁹, —OCOR⁹, CONR⁹R¹⁰, —NR⁹R¹⁰, —N(COR⁹)R¹⁰, —SO₂R⁹, —SO₂NR⁹R¹⁰;

R¹² is selected from the group consisting of —OR⁹, —COR⁹, —COOR⁹, —OCOR⁹, —CONR⁹R¹⁰, —NR⁹R¹⁰, —N(COR⁹)R¹⁰, —SO₂R⁹, —SO₂NR⁹R¹⁰, halogen, —CN, —NO₂, perfluoroalkyl; and X is selected from the group consisting of —N— and —C—.

2. A compound of formula

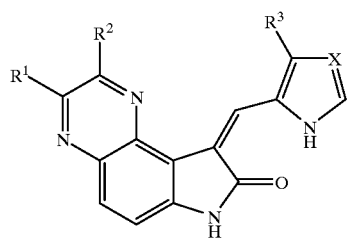

I or the pharmaceutically acceptable salts of the foregoing compounds, wherein:

R¹ and R² are independently selected from the group consisting of
—H,
OR⁴,
—COR⁴,
—COOR⁴,
—CONR⁵R⁶,
—NR⁵R⁶, lower alkyl which optionally may be substituted by the group consisting of —OR⁴, —NR⁵R⁶, halogen, —COR⁴, —COOR⁴, —OCOR⁴, —CONR⁵R⁶, —CN, —SO₂R⁴, —SO₂NR⁵R⁶, cycloalkyl, heterocycle, aryl, and heteroaryl, wherein the cycloalkyl and heterocycle each may be optionally substituted by the group R¹¹ and the aryl and heteroaryl each may be optionally substituted by the group R¹², cycloalkyl which optionally may be substituted by the group consisting of —OR⁴, —NR⁵R⁶, halogen, —COR⁴, —COOR⁴, —OCOR⁴, —CONR⁵R⁶, —CN, —SO₂R⁴, —SO₂NR⁵R⁶, lower alkyl, heterocycle, aryl, and heteroaryl, wherein the lower all and heterocycle each may be optionally substituted by the group R¹¹ and the aryl and heteroaryl each may be optionally substituted by the group R¹², heterocycle which optionally may be substituted by the group consisting of —OR⁴, —NR⁵R⁶, halogen, —COR⁴, —COOR⁴, —OCOR⁴, —CONR⁵R⁶, —CN, —SO₂R⁴, —SO₂NR⁵R⁶, lower alkyl, cycloalkyl, aryl, and heteroaryl, wherein the lower alkyl and cycloalkyl each may be optionally substituted by the group R¹¹ and the aryl and heteroaryl each may be optionally substituted by the group R¹², aryl which optionally may be substituted by the group consisting of —OR⁴, —NR⁵R⁶, halogen, —NO₂, perfluoroalkyl, —COR⁴, —COOR⁴, —OCOR⁴, —CONR⁵R⁶, —CN, —SO₂R⁴, —SO₂NR⁵R⁶, lower alkyl, cycloalkyl, heterocycle, aryl, and heteroaryl, and wherein the lower alkyl, cycloalkyl and heterocycle each may be optionally substituted by the group R¹¹ and the aryl and heteroaryl each may be optionally substituted by the group R¹², heteroaryl which optionally may be substituted by the group consisting of —OR⁴, —NR⁵R⁶, halogen, —NO₂, perfluoroalkyl, —COR⁴, —COOR⁴, —OCOR⁴, —CONR⁵R⁶, —CN, —SO₂R⁴, —SO₂NR⁵R⁶, lower alkyl, cycloalkyl, heterocycle, aryl, and heteroaryl and wherein the lower alkyl, cycloalkyl and heterocycle each may be optionally substituted by the group R¹¹ and the aryl and heteroaryl each may be optionally substituted by the group $R^{12}$, or alternatively, $R^1$ and $R^2$ optionally can form a ring having 5–7 atoms, said ring optionally including one or more heteroatoms and being optionally substituted by the group consisting of —$OR^8$, —$COR^7$, —$COOR^7$, —$CONR^7R^9$, —$NR^8R^9$, and lower alkyl which optionally may be substituted by the group $R^{11}$;

$R^3$ is selected from the group consisting of
—H
$OR^4$
—$COR^4$
—$COOR^4$
—$OCOR^4$
—$CONR^5R^6$
halogen
—CN
perfluoroalkyl
—$NR^5R^6$, and
lower alkyl which optionally may be substituted by —$OR^4$, —$OCOR^4$, or —$NR^5R^6$;

$R^4$ is selected from the group consisting of
—H,
lower alkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$, heterocycle which optionally may be substituted by the group consisting of —$OR^8$, —$COOR^7$, —$COR^7$, —$CONR^5R^6$, —$NR^5R^6$, —$SO_2R^7$, —$SO_2NR^5R^6$, cycloalkyl, lower alkyl, aryl, and heteroaryl, and wherein the cycloalkyl and lower alkyl each may be optionally substituted by the group $R^{11}$ and the aryl and heteroaryl each may be optionally substituted by the group $R^{12}$, aryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, lower alkyl, cycloalkyl, heterocycle, aryl, and heteroaryl, and wherein the lower alky, cycloalkyl and heterocycle each may be optionally substituted by the group $R^{11}$ and the aryl and heteroaryl each may be optionally substituted by the group $R^{12}$, and heteroaryl which optionally may be substituted by the group consisting of —$OR^8$, —$COOR^7$, —$COR^7$, —$CONR^5R^6$, —$NR^5R^6$, —$NO_2$, halogen, perfluoroalkyl, —$SO_2R^7$, —$SO_2NR^5R^6$, cycloalkyl, lower alkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$;

$R^5$ and $R^6$ are each independently selected from the group consisting of
—H,
—$COR^7$,
—$COOR^7$,
—$CONR^7R^9$, and
lower alkyl which optionally may be substituted by the group consisting of —$OR^8$, —$COOR^7$, —$COR^7$, —$CONR^7R^8$, —$NR^7R^8$, —$SO_2R^7$, —$SO_2NR^7R^8$, cycloalkyl, heterocycle, aryl, and heteroaryl, and wherein the cycloalkyl and heterocycle each may be optionally substituted by the group $R^{11}$ and the aryl and heteroaryl each may be optionally substituted by the group $R^{12}$, cycloalkyl which optionally may be substituted by the group consisting of —$OR^8$, —$COOR^7$, —$COR^7$, —$CONR^7R^8$, —$NR^7R^8$, —$SO_2R^7$, —$SO_2NR^7R^8$, lower alkyl, heterocycle, aryl, and heteroaryl, and wherein the lower alkyl and heterocycle each may be optionally substituted by the group $R^{11}$ and the aryl and heteroaryl each may be optionally substituted by the group $R^{12}$, heterocycle which optionally may be substituted by the group consisting of —$OR^8$, —$COOR^7$, —$COR^7$, —$CONR^7R^8$, —$NR^7R^8$, —$SO_2R^7$, —$SO_2NR^7R^8$, cycloalkyl, lower alkyl, aryl, and heteroaryl, and wherein the cycloalkyl and lower alyl each may be optionally substituted by the group $R^{11}$ and the aryl and heteroaryl each may be optionally substituted by the group $R^{12}$, aryl which optionally may be substituted by the group consisting of $OR^8$, —$COOR^7$, —$COR^7$, —$CONR^7R^8$, —$NR^7R^8$, —$NO_2$, halogen, perfluoroalkyl, —$SO_2R^7$, —$SO_2NR^7R^8$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$, and heteroaryl which optionally may be substituted by the group consisting of —$OR^8$, —$COOR^7$, —$COR^7$, —$CONR^7R^8$, —$NR^7R^8$, —$NO_2$, halogen, perfluoroalkyl, —$SO_2R^7$, —$SO_2NR^7R^8$, lower alkyl, cycloalkyl, heterocycle, aryl, and heteroaryl, and wherein the lower alkyl, cycloalkyl and heterocycle each may be optionally substituted by the group $R^{11}$ and the aryl and heteroaryl each may be optionally substituted by the group $R^{12}$; or alternatively, —$NR^5R^6$ can optionally form a ring having 3 to 7 atoms, said ring optionally including one or more additional hetero atoms and being optionally substituted by the group consisting of lower alkyl, —$OR^8$, —$COR^7$, —$COOR^7$, —$CONR^7R!$, and —$NR^8R^9$;

$R^7$ is selected from the group consisting of
—H, and
lower alkyl which optionally may be substituted by the group consisting of cycloalkyl, heterocycle, aryl, heteroaryl, —$OR^9$, and —$NR^8R^9$;

$R^8$ is selected from the group consisting of
—H,
—$COR^9$,
—$CONR^{10}R^9$, and
lower alkyl which optionally may be substituted by $R^{11}$;

$R^9$ and $R^{10}$ are each independently selected from the group consisting of —H and lower alkyl;

$R^{11}$ is selected from the group consisting of —$OR^9$, —$COR^9$, —$COOR^9$, —$OCOR^9$, —$CONR^9R^{10}$, —$NR^9R^{10}$, —$N(COR)R^{10}$, —$SO_2R^9$, —$SO_2NR^9R^{10}$;

$R^{12}$ is selected from the group consisting of —$OR^9$, —$COR^9$, —$COOR^9$, —$OCOR^9$, —$CONR^9R^{10}$, —$NR^9R^{10}$, —$N(COR^9)R^{10}$, —$SO_2R^9$, —$SO_2NR^9R^{10}$, halogen, —CN, —$NO_2$, perfluoroalkyl; and X is selected from the group consisting of —N— and —C—.

3. The compound of claim 2 wherein $R^3$ is selected from the group consisting of

—H, $OR^4$,

—$NR^5R^6$, and lower alkyl which optionally may be substituted by the group consisting of —$OR^4$ and —$NR^5R^6$.

4. The compound of claim 2 wherein X is —C—.

5. The compound of claim 1 wherein $R^3$ is selected from the group consisting of

—H,

—$OR^4$,

—$NR^5R^6$, and lower alkyl which optionally may be substituted by the group consisting of —$OR^4$ and —$NR^5R^6$.

6. The compound of claim 1 wherein X is —C—.

7. A compound selected from the group consisting of:

(Z)-7,9-Dihydro-2,3-dimethyl-9[(3-methoxy-1H-pyrrol-2-yl)methylene]-8H-pyrrolo-[3,2-f]quinoxaline-8-one (A), (Z)-3-Butyl-7,9-dihydro-9-[(3-methoxy-1H-pyrrol-2-yl)methylene]-2-methyl-8H-pyrrolo[3,2-f]quinoxalin-8-one and (Z)-2-butyl-7,9-dihydro-9-[(3-methoxy-1H-pyrrol-2-yl)methylene]-3-methyl-8H-pyrrolo[3,2-f]quinoxalin-8-one (B), (Z)-7,9-Dihydro-9-[(3-methoxy-1H-pyrrol-2-yl)methylene]-2-methyl-3-phenyl-8H-pyrrolo[3,2-f]quinoxalin-8-one and (Z)-7,9-dihydro-9-[(3-methoxy-1H-pyrrol-2-yl)methylene]-3-methyl-2-phenyl-8H-pyrrolo[3,2-f]quinoxalin-8-one (C), (Z)-7,9-Dihydro-2,3-di-(2-furanyl)-9-[(3-methoxy-1H-pyrrol-2-yl)methylene]-8H-pyrrolo[3,2-f]quinoxalin-8-one (D), and (Z)-1,3,5,6,7,8-Hexahydro-3-[(3-methoxy-1H-pyrrol-2-yl)methylene]-2H-pyrrolo[3,2-a]phenazin-2-one (E).

8. A pharmaceutical composition comprising as an active ingredient an effective amount of a compound of claim 2 and a pharmaceutically acceptable carrier or excipient.

9. A pharmaceutical composition comprising as an active ingredient an effective amount of a compound of claim 1 and a pharmaceutically acceptable carrier or excipient.

10. A pharmaceutical composition comprising as an active ingredient an effective amount of a compound of claim 3 and a pharmaceutically acceptable carrier or excipient.

11. A pharmaceutical composition comprising as an active ingredient an effective amount of a compound of claim 7.

12. The pharmaceutical composition of claim 8 which is suitable for parenteral administration.

13. The pharmaceutical composition of claim 11 which is suitable for parenteral administration.

14. A method for treating rheumatoid arhritis comprising administering to a subject in need thereof of a therapeutically effective amount of a compound according to claim 1.

15. A method for treating rheumatoid arthritis comprising administering to a subject in need thereof of a therapeutically effective amount of a compound according to claim 2.

16. A method for treating rheumatoid arthritis comprising administering to a subject in need thereof of a therapeutically effective amount of a compound according to claim 7.

\* \* \* \* \*

UNITED STATES PATENT AND TRADEMARK OFFICE
CERTIFICATE OF CORRECTION

PATENT NO.   : 6,221,867 B1
DATED        : April 24, 2001
INVENTOR(S)  : Luk, et al.

It is certified that error appears in the above-identified patent and that said Letters Patent is hereby corrected as shown below:

Column 24, claim 1,
Line 46, "cycloallyl" should read -- cycloalkyl --.

Column 25, claim 1,
Line 35, "alky," should read -- alkyl, --.

Column 28, claim 2,
Line 27, "alyl" should read -- alkyl --.
Line 54, "-CONR$^7$R!" should read -- -CONR$^7$R$^9$ --.

Column 29, claim 7,
Line 30, "quinoxaline" should read -- quinoxalin --.

Column 30, claim 14,
Line 26, "arhritis" should read -- arthritis --.

Signed and Sealed this

Sixth Day of November, 2001

Attest:

*Nicholas P. Godici*

NICHOLAS P. GODICI
*Attesting Officer*   *Acting Director of the United States Patent and Trademark Office*